US012758171B2

(12) United States Patent
Mazumder et al.

(10) Patent No.: US 12,758,171 B2
(45) Date of Patent: Oct. 13, 2026

(54) METHOD AND SYSTEM FOR SOURCE LOCALIZATION OF ATRIAL FIBRILLATION

(71) Applicant: Tata Consultancy Services Limited, Mumbai (IN)

(72) Inventors: Oishee Mazumder, Kolkata (IN); Aniruddha Sinha, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 94 days.

(21) Appl. No.: 18/953,978

(22) Filed: Nov. 20, 2024

(65) Prior Publication Data

US 2025/0169783 A1 May 29, 2025

(30) Foreign Application Priority Data

Nov. 28, 2023 (IN) ............................ 202321080595

(51) Int. Cl.
*A61B 6/50* (2024.01)
*A61B 6/00* (2024.01)
(Continued)

(52) U.S. Cl.
CPC ............ *A61B 6/503* (2013.01); *A61B 6/5217* (2013.01); *A61B 6/5258* (2013.01);
(Continued)

(58) Field of Classification Search
CPC ..... A61B 6/503; A61B 6/5217; A61B 6/5258; G06V 10/25; G06V 10/30; G06V 10/26;
(Continued)

(56) References Cited

U.S. PATENT DOCUMENTS 11,540,879 B2 1/2023 Bort et al.
2015/0230721 A1* 8/2015 Lo ......................... A61B 5/367 600/512

(Continued)

OTHER PUBLICATIONS

Atienza, F., et al. "Real-time Dominant Frequency Mapping and Ablation of Dominant-Frequency Sites in Atrial Fibrillation with Left-to-Right Frequency Gradients Predicts Long-Term Maintenance of Sinus Rhythm," Heart Rhythm. vol. 6(1), 2009. p. 33-40 (Year: 2009).*

(Continued)

*Primary Examiner* — Sean A Frith
(74) *Attorney, Agent, or Firm* — Finnegan, Henderson, Farabow, Garrett & Dunner LLP

(57) ABSTRACT

Conventionally, invasive techniques are used to localize Atrial Fibrillation sources, but they are inconvenient, technically complex, and expensive. Non-invasive methods such as ECGI are prone to errors due to small volume and wall thickness of the atria. Thus, embodiments of present disclosure provide a method and system for source localization of AF utilizing a modified dominant frequency approach and atrium depolarization time. The method initially obtains heart and torso scan images and extracts atrial and torso meshes from them. Then, Body Surface Potential (BSP) signals are sampled from the atrial meshes and torso meshes. Cardiac potential is reconstructed from BSP. Further, AF-DF probability and probable rotor regions are determined from the cardiac potential. AF sources are then localized by combining AF-DF probability and probable rotor regions. Thus, the disclosed method which is non-invasive can be used for patient stratification for AF treatment plan, personalize procedure planning, and reduce ablation time.

12 Claims, 8 Drawing Sheets

(51) Int. Cl.
*G06T 7/00* (2017.01)
*G06V 10/25* (2022.01)
*G06V 10/26* (2022.01)
*G06V 10/30* (2022.01)

(52) U.S. Cl.
CPC ............ *G06T 7/0016* (2013.01); *G06V 10/25* (2022.01); *G06V 10/26* (2022.01); *G06V 10/30* (2022.01); *G06T 2207/20076* (2013.01); *G06T 2207/30048* (2013.01); *G06V 2201/031* (2022.01)

(58) Field of Classification Search
CPC ............ G06V 2201/031; G06T 7/0016; G06T 2207/20076; G06T 2207/30048
See application file for complete search history.

(56) References Cited

U.S. PATENT DOCUMENTS

| | | | | |
|---|---|---|---|---|
| 2017/0255745 | A1* | 9/2017 | Mihalef | G16H 10/60 |
| 2019/0104962 | A1* | 4/2019 | Ghoraani | A61B 5/7282 |
| 2019/0223819 | A1* | 7/2019 | Mansi | G06T 15/205 |

OTHER PUBLICATIONS

Ferrer, A., "Detailed Anatomical and Electrophysiological Models of Human Atria and Torso for the Simulation of Atrial Activation," PLOS ONE. 2015. p. 1-29 (Year: 2015).*

Kong, F., et al. "Learning Whole Heart Mesh Generation From Patient Images for Computational Simulations," IEEE Transactions on Medical Imaging. vol. 42(2), 2023. p. 533-545 (Year: 2023).*

Bergquist, J., et al. "Body Surface Potential Mapping: Contemporary Applications and Future Perspectives," Hearts (Basel). vol 2(4), 2021. p. 514-542 (Year: 2021).*

Cámara-Vázquez et al., "Non-invasive Estimation of Atrial Fibrillation Driver Position With Convolutional Neural Networks and Body Surface Potentials," Frontiers in Physiology, 12:733449 (2021).

Rodrigo et al., "Non-invasive Spatial Mapping of Frequencies in Atrial Fibrillation: Correlation With Contact Mapping," Frontiers in Physiology, 11:611266 (2021).

* cited by examiner

METHOD AND SYSTEM FOR SOURCE LOCALIZATION OF ATRIAL FIBRILLATION

PRIORITY CLAIM

This U.S. patent application claims priority under 35 U.S.C. § 119 to: Indian Patent Application No. 202321080595, filed on Nov. 28, 2023. The entire contents of the aforementioned application are incorporated herein by reference.

TECHNICAL FIELD

The disclosure herein generally relates to the field of noninvasive estimation of atrial fibrillation source, and, more particularly, to a method and system for source localization of atrial fibrillation using probabilistic dominant frequency and spatiotemporal depolarization time.

BACKGROUND

Atrial fibrillation (AF) is a chronic arrhythmic disorder characterized by chaotic electrical activation of the atria, resulting in altered P wave, which is often absent and substituted by low amplitude and irregular atrial waves. This leads to inefficient blood pumping, increasing the risk of embolism, stroke, and cardiac failure. Clinical management of AF focuses on restoring sinus rhythm in the atria by pharmacological means or ablation of cardiac tissue responsible for arrhythmogenesis, but both approaches have sub-optimal outcome in correcting AF. Location of arrhythmic sources are conventionally identified via an electrophysiological (EP) study, which is an invasive method, involving multiple catheters introduced in the atrial chambers to map the intracardiac signals. Local activation time (LAT) derived from signals captured by such catheters serve as a metric to identify arrhythmic sources. Such EP study is technically complex and expensive, demanding a large amount of time. Also, the complex atrial geometry and low spatial resolution of catheters limits proper electrical activity characterization of AF. Animal experiments and mapping studies have shown that chaotic and disorganized AF propagation are actually driven by rotors or focal drivers that are areas with high frequency depolarization. These drivers can originate anywhere in the atrium, mostly near scar or fibrosis cells.

ECGI (Electrocardiographic Imaging) is a recent approach towards non-invasive generation of cardiac activation maps for arrhythmic source localization that has gained immense research and medical interests. ECGI solves the inverse electrophysiology problem by reconstructing cardiac potential from torso or Body Surface Potential (BSP) using the 3D torso-cardiac structure segmented from Computed Tomography (CT) or Magnetic Resonance Imaging (MRI) scans and some numerical methods and regularization algorithms. ECGI techniques and advanced signal processing involving atrial potential, dominant frequency and phase based analysis have been used in recent years to locate arrhythmia driving sources and improve ablation outcomes. However, characterization of electrical propagation in AF is difficult due to small volume and wall thickness of the atria, remodeling of the myocardium structure, errors due to ECGI regularization and functional collision of fibrillatory waves that creates high frequency values not associated with arrhythmic source. Some other prior arts use deep learning methods to detect source of AF from CT/MRI scans, but they require huge amount of training data to train neural networks.

SUMMARY

Embodiments of the present disclosure present technological improvements as solutions to one or more of the above-mentioned technical problems recognized by the inventors in conventional systems. For example, in one embodiment, a method for source localization of atrial fibrillation is provided. The method includes obtaining a plurality of heart scan images and a plurality of torso scan images and extracting a) one or more atrial meshes from the plurality of heart scan images, and b) one or more torso meshes from the plurality of torso scan images. Further, the method includes sampling one or more Body Surface Potential (BSP) signals from the one or more torso meshes and the one or more atrial meshes and determining a cardiac potential from the one or more BSP signals. The method further includes identifying one or more probable rotor regions in the one or more atrial meshes based on the cardiac potential. Further, the method includes determining an Atrial Fibrillation-Dominant Frequency (AF-DF) probability based on the cardiac potential. Furthermore, the method includes determining a net probability of localizing AF source in the one or more atrial meshes by combining the identified one or more probable rotor regions and the AF-DF probability. The one or more atrial meshes having a net probability exceeding a threshold of net probability indicate locations of source of atrial fibrillation.

In another aspect, a system for source localization of atrial fibrillation is provided. The system includes a memory storing instructions; one or more communication interfaces; and one or more hardware processors coupled to the memory via the one or more communication interfaces, wherein the one or more hardware processors are configured by the instructions to: obtain a plurality of heart scan images and a plurality of torso scan images and extract a) one or more atrial meshes from the plurality of heart scan images, and b) one or more torso meshes from the plurality of torso scan images. Further, the one or more hardware processors are configured to sample one or more Body Surface Potential (BSP) signals from the one or more torso meshes and the one or more atrial meshes and determine a cardiac potential from the one or more BSP signals. The one or more hardware processors are further configured to identify one or more probable rotor regions in the one or more atrial meshes based on the cardiac potential. Further, the one or more hardware processors are configured to determine an Atrial Fibrillation-Dominant Frequency (AF-DF) probability based on the cardiac potential. Furthermore, the one or more hardware processors are configured to determine a net probability of localizing AF source in the one or more atrial meshes by combining the identified one or more probable rotor regions and the AF-DF probability. The one or more atrial meshes having a net probability exceeding a threshold of net probability indicate locations of source of atrial fibrillation.

In yet another aspect, there are provided one or more non-transitory machine-readable information storage mediums comprising one or more instructions which when executed by one or more hardware processors cause a method for source localization of atrial fibrillation. The method includes obtaining a plurality of heart scan images and a plurality of torso scan images and extracting a) one or more atrial meshes from the plurality of heart scan images, and b) one or more torso meshes from the plurality of torso scan images. Further, the method includes sampling one or more Body Surface Potential (BSP) signals from the one or more torso meshes and the one or more atrial meshes and determining a cardiac potential from the one or more BSP signals. The method further includes identifying one or more probable rotor regions in the one or more atrial meshes based on the cardiac potential. Further, the method includes determining an Atrial Fibrillation-Dominant Frequency (AF-DF) probability based on the cardiac potential. Furthermore, the method includes determining a net probability of localizing AF source in the one or more atrial meshes by combining the identified one or more probable rotor regions and the AF-DF probability. The one or more atrial meshes having a net probability exceeding a threshold of net probability indicate locations of source of atrial fibrillation.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
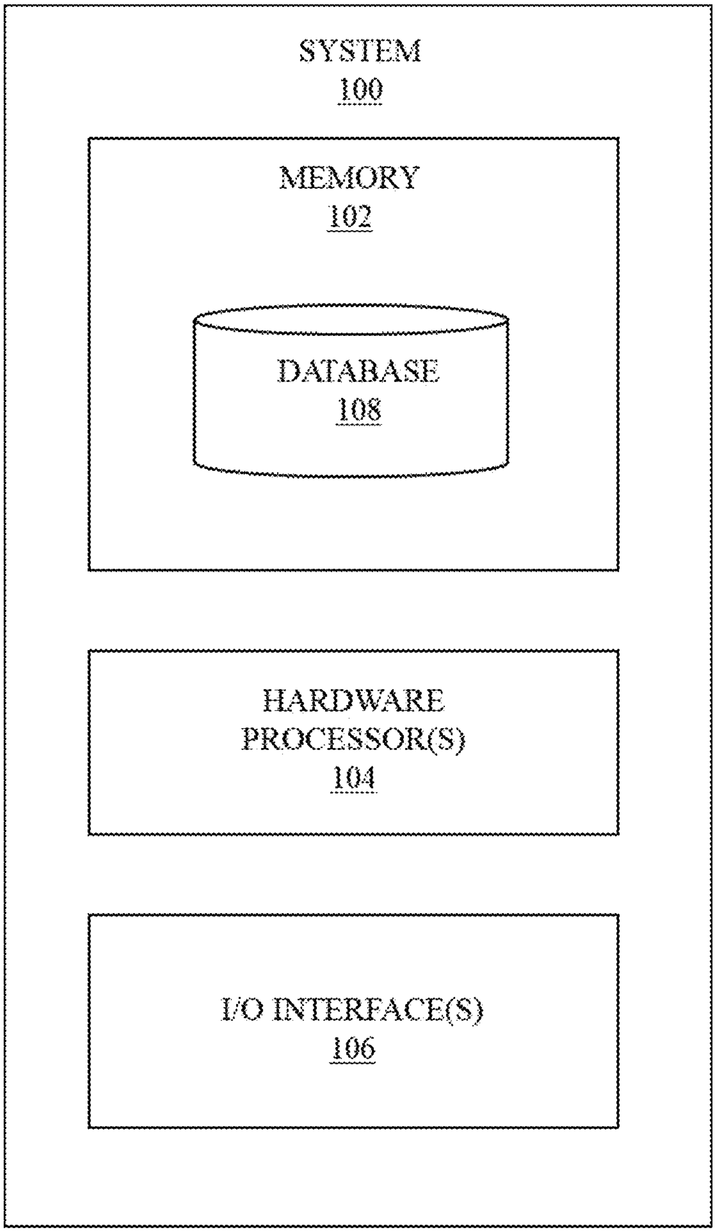
FIG. 1 illustrates an exemplary system for source localization of atrial fibrillation, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Atrial fibrillation (AF) is a common cardiac arrhythmia with high prevalence and morbidity. AF can be managed by ablation therapy, where AF driving sources are identified and ablated to restore sinus rhythm. Conventionally, invasive techniques are used to localize AF sources, but they are inconvenient, technically complex, and expensive. Non-invasive methods such as ECGI are prone to errors due to small volume and wall thickness of the atria. In order to overcome the aforementioned technical challenges in state of the art techniques, embodiments of present disclosure provide a method and system for source localization of atrial fibrillation utilizing a modified dominant frequency approach and atrium depolarization time using spatiotemporal activation. The method initially obtains heart scan and torso scan images and extracts atrial meshes and torso meshes from them. Then, Body Surface Potential (BSP) signals are sampled from the atrial meshes and torso meshes. A cardiac potential is determined from the BSP signals from which AF-DF probability and probable rotor regions are computed. Finally, the probable AF sources are identified by combining both AF-DF probability and probable rotor regions.

Referring now to the drawings, and more particularly to FIGS. 1 to 7B, where similar reference characters denote corresponding features consistently throughout the figures, there are shown preferred embodiments and these embodiments are described in the context of the following exemplary system and/or method.

FIG. 1 illustrates an exemplary block diagram of a system for source localization of atrial fibrillation, according to some embodiments of the present disclosure. In an embodiment, the system 100 includes one or more processors (104), communication interface device(s) (106) or Input/Output (I/O) interface(s) (106) or user interface (106), and one or more data storage devices or memory (102) operatively coupled to the one or more processors (104). The one or more processors (104) that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud, and the like.

The I/O interface device(s) (106) can include a variety of software and hardware interfaces, for example, a web interface, a graphical user interface, and the like and can facilitate multiple communications within a wide variety of networks and protocol types, including wired networks, for example, LAN, cable, etc., and wireless networks, such as WLAN, cellular, or satellite. In an embodiment, the I/O interface device(s) (106) receives heart scan images and torso scan images and provides probable locations of source of Atrial Fibrillation as output. The memory (102) may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The database 108 stores information pertaining to inputs fed to the system 100 and/or outputs generated by the system (e.g., at each stage), specific to the methodology described herein. Functions of the components of system 100 are explained in conjunction with flow diagram depicted in FIG. 2, block diagram illustrated in FIG. 3 and results illustrated in FIGS. 4 to 7B for source localization of atrial fibrillation.

Figure 2:
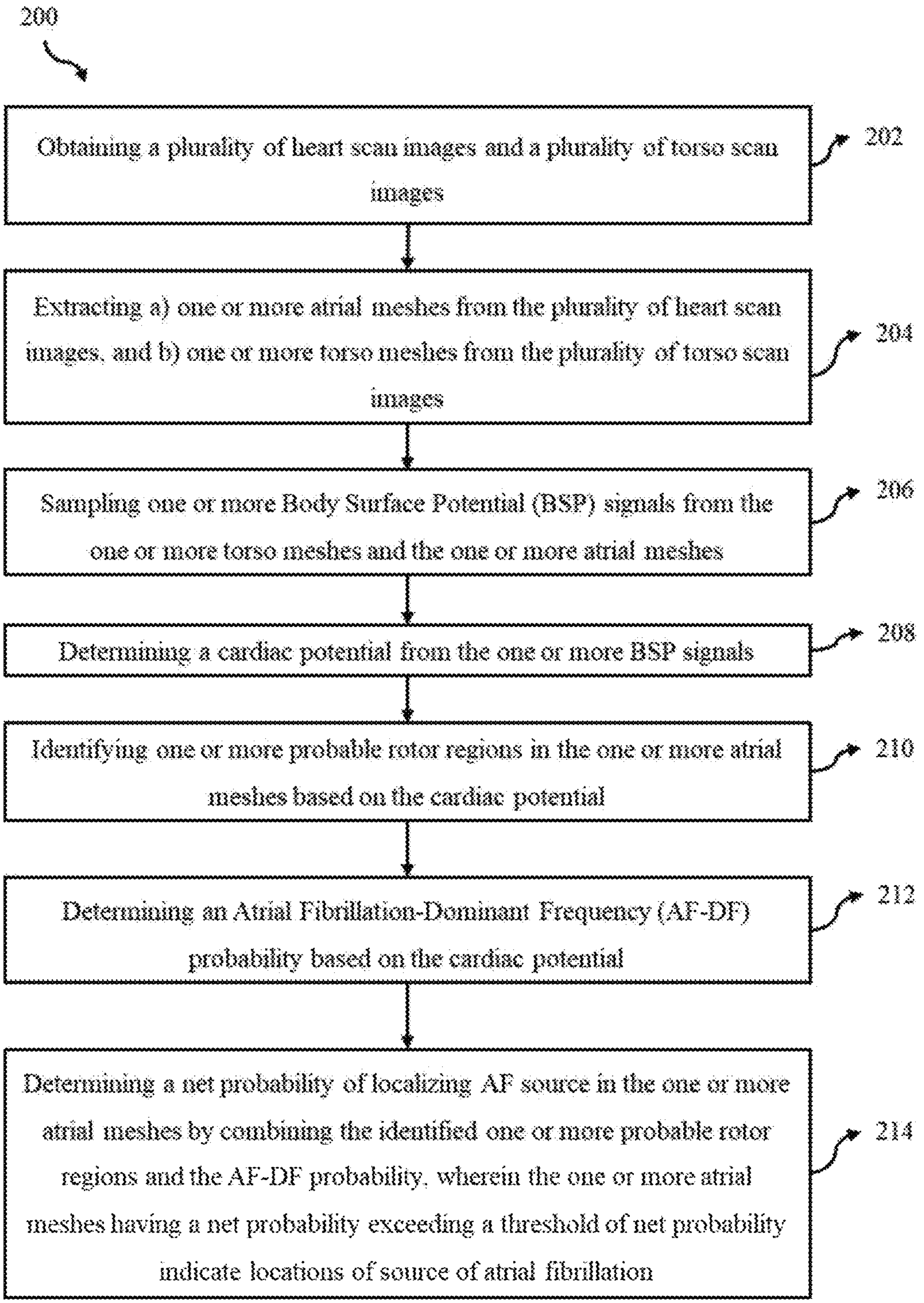
FIG. 2 illustrates a flow diagram of a processor implemented method for source localization of atrial fibrillation, according to some embodiments of the present disclosure.
Figure 3:
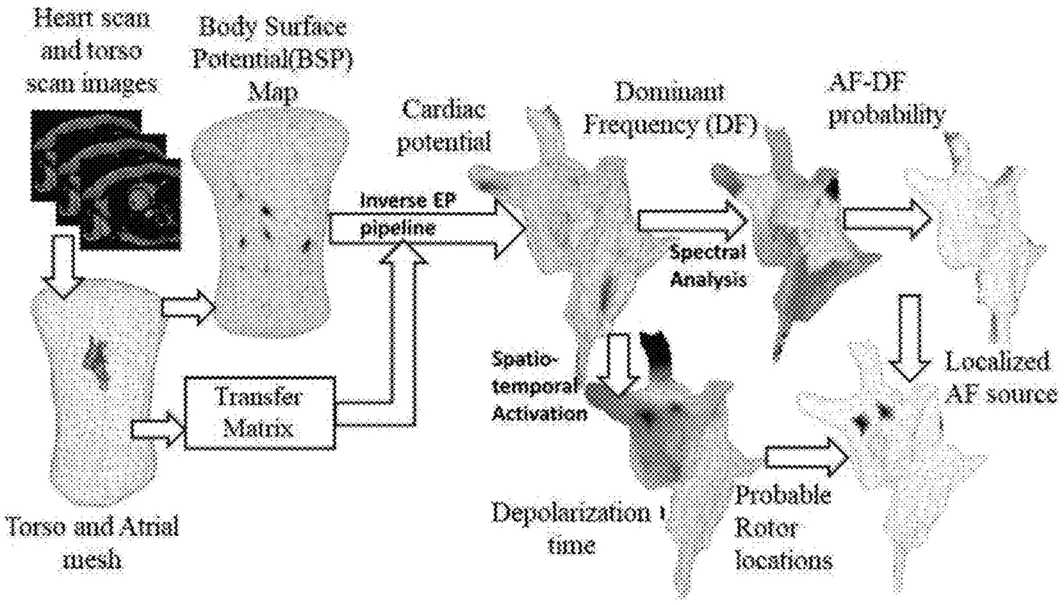
FIG. 3 illustrates a block diagram of the method illustrated in FIG. 2 for source localization of atrial fibrillation, according to some embodiments of the present disclosure.

In an embodiment, the system 100 comprises one or more data storage devices or the memory (102) operatively coupled to the processor(s) (104) and is configured to store instructions for execution of steps of the method (200) depicted in FIG. 2 by the processor(s) or one or more hardware processors (104). The steps of the method of the present disclosure will now be explained with reference to the components or blocks of the system 100 as depicted in FIG. 1, the steps of flow diagrams as depicted in FIG. 2, block diagram illustrated in FIG. 3 and results illustrated in FIGS. 4 to 7B. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

FIG. 2 is a flow diagram of a method 200 for source localization of atrial fibrillation, according to some embodiments of the present disclosure. The method 200 is explained in conjunction with block diagram of FIG. 3. At step 202 of the method 200, the one or more hardware processors 104 are configured to obtain a plurality of heart scan images and a plurality of torso scan images using techniques such as Computed Tomography (CT), Magnetic Resonance Imaging (MRI) scanning techniques and the like. Further, at step 204 of the method 200, the one or more hardware processors 104 are configured to extract a) one or more atrial meshes from the plurality of heart scan images, and b) one or more torso meshes from the plurality of torso scan images using tools such as tetrgen, biomesh and the like. Further, at step 206 of the method 200, the one or more hardware processors 104 are configured to sample one or more Body Surface Potential (BSP) signals from the one or more torso meshes and the one or more atrial meshes. In an embodiment, the one or more BSP signals are pre-processed by first segregating them into a plurality of consecutive time windows. Then, noise is removed from the one or more BSP signals in each of the plurality of consecutive time windows using a notch filter. Finally, baseline wandering is removed from the one or more BSP signals in each of the plurality of consecutive time windows using a multilevel 1-dimensional (1D) wavelet decomposition technique. Any other pre-processing techniques such as smoothing, filtering etc., maybe applied on the BSP signals in different embodiments.

Once the one or more BSP signals are pre-processed, at step 208 of the method 200, the one or more hardware processors 104 are configured to determine a cardiac potential (alternatively referred as atrial potential) from the one or more BSP signals using Inverse computed atrial EGM (icEGM) technique by solving the inverse problem of electrocardiography. icEGM is based on Maxwell's electromagnetic theory. According to Maxwell's electromagnetic wave equation, the potential measured at the torso surface ($\phi_T$) is computed according to equation 1, where $B_{TC}$ is a transfer matrix (illustrated in FIG. 3) defining the geometric relation between the 3D surfaces of the torso and heart, and Pc is the cardiac potential. In inverse problem, (Pc cannot be computed from $\phi_T$ as $(B_{TC})^{-1}\phi_T$ since the inverse solution is ill-posed. Regularization methods are used to force a unique and smooth solution. In an embodiment, zero order Tikhonov regularization is used to determine the cardiac potential since it performs relatively well under fibrillatory conditions. Any other regularization methods maybe used in different embodiments. The Tikhonov regularized solution is obtained by minimizing the objective function given in equation 2. The first term in right hand side of the equation 2 is the L2 squared error and the second term comprises Tikhonov matrix R (identity matrix for zero order Tikhonov) and regularization parameter λ which regularizes the solution in spatial plane. The transfer matrix $B_{TC}$ is computed by simulating signal propagation between the one or more atrial meshes and the one or more torso meshes using boundary element method.

$$\phi_T = B_{TC}\phi_C \tag{1}$$

$$\phi_C = \min\left[\|B_{TC} - \phi_T\|_2^2 + \lambda\|R\phi_C\|_2^2\right. \tag{2}$$

Once the cardiac potential is determined, at step 210 of the method 200, the one or more hardware processors 104 are configured to identify one or more probable rotor regions in the one or more atrial meshes based on the cardiac potential. The one or more probable rotor regions are identified based on a depolarization time (alternatively referred as activation time) which is computed from the cardiac potential. The depolarization time captures time course of an entire beat in single isochronal map. During AF, depolarization time increases due to increase in late component of the cardiac Na+ current (Ina, L) caused by increase in Na+ permeability. Sites showing late or increased depolarization during AF may be regarded as probable rotor regions (alternatively referred as rotor sites or rotor areas). Activation time at which the temporal behavior of depolarization occurs is computed from the cardiac potential $\phi_C$ by determining the most negative temporal derivative of each atrial node in the one or more atrial meshes. For complex surface like cardiac chambers, only temporal derivatives introduce errors, mostly when dealing with fractionated electrograms (EGM). It can be overcome by spatial computation of activation time, determined by implementing Laplacian of the cardiac potential, where the second order spatial derivative changes sign at the time of activation (depolarization). Combining both temporal and spatial derivatives, depolarization time is estimated from signals that have sharp changes in electric potential values in both time and space simultaneously. Computation of depolarization time can be mathematically represented by equation 3, wherein τ is the depolarization time, $\partial\phi(t)/\partial t$ is the temporal derivative and $M\phi(t)$ is the spatial derivative. The resultant depolarization time is then smoothed by minimizing the function given in equation 4.

$$\tau = \min\|M\phi(t)\|_2, \frac{\partial\phi(f)}{\partial t} \tag{3}$$

$$\min_{\tau_D}\|\tau - \tau_D\|_2^2 + \gamma\left\|L_{\tau_D}\right\|_2^2 \tag{4}$$

The first term in equation 4 is a least square minimization with respect to pre-smoothing estimation and the second term minimizes the surface Laplacian of the estimate. L is the Laplace operator. These two terms are balanced using parameter γ. For small value of γ, smoothing effect is low while for high value, resulting time estimate tends to zero. The smoothed depolarization time is then normalized. The one or more atrial meshes having normalized value of the computed depolarization time greater than a predefined threshold value are identified as the one or more probable rotor regions.

Further, at step 212 of the method 200, the one or more hardware processors 104 are configured to determine an Atrial Fibrillation-Dominant Frequency (AF-DF) probability based on the cardiac potential. Firstly, a Power Spectral Density (PSD) is estimated from the cardiac potential. Then, frequency values in the PSD are arranged in descending order. The peak or highest frequency value is considered as dominant frequency. To increase reliability of detecting peak power representing DF, a Regularity Index (RI) is computed as the ratio of the power at the DF and its adjacent frequencies (0.75-Hz band) to the power of the 3- to 15-Hz band. A high value of RI indicates high reliability, which means that the frequency peak under consideration makes a greater contribution to the selected frequency range. Then, the AF-DF probability is calculated as normalized value of ratio of power at a peak frequency and power at a second peak frequency in the PSD. The AF-DF probability metric further reduces errors in DF localization due to fibrillatory wave wandering, poor signal to noise ratio or errors due to geometric approximation.

Once the one or more probable rotor regions and AF-DF probability are determined, at step 214 of the method 200, the one or more hardware processors 104 are configured to determine a net probability of localizing AF source in the one or more atrial meshes by combining the identified one or more probable rotor regions and the AF-DF probability. The one or more atrial meshes having a net probability exceeding a threshold of net probability indicate locations of source of atrial fibrillation.

Figure 4:
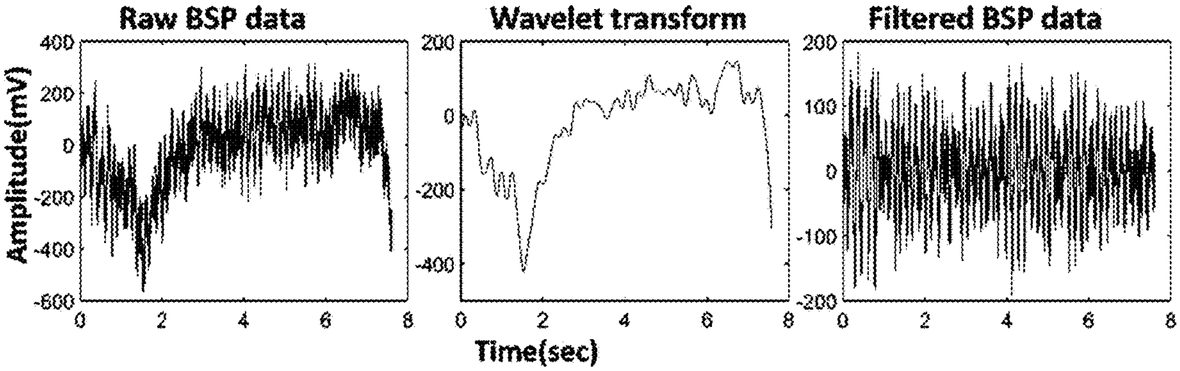
FIG. 4 illustrates result of pre-processing Body Surface Potential (BSP) signals, according to some embodiments of the present disclosure.
Figure 5:
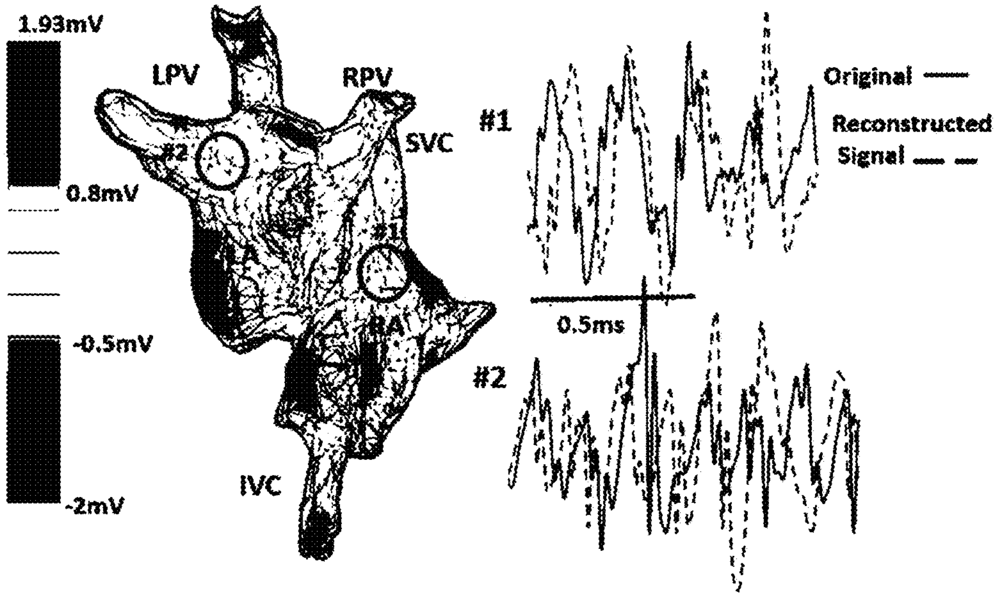
FIG. 5 illustrates an example cardiac potential measurement along with key anatomical areas of the atrium, according to some embodiments of the present disclosure.

USE CASE EXAMPLE: The method 200 was performed on AF subject data from Experimental Data and Geometric Analysis Repository (EDGAR) database (contributed by Universität Politcnica de Valencia, Valencia, Spain). This dataset contains signals and geometrical meshes from 2 AF patients scheduled for an ablation procedure. BSP signals were recorded from 54 leads covering the torso. Ventricular activities were blocked by adenosine bolus infusion to record only the atrial contribution. Endocardial signals from 64 pole basket catheter located sequentially on the right and left atria were also recorded. The torso and atrial meshes extracted from patient MRI consisted of 2002 and 1998 nodes respectively. Sampling frequency for both BSP and endocardial signals were 2 kHz. 54 channel BSP signals were preprocessed as follows: 7.5 seconds long signals were segregated into 6 consecutive windows of 2 seconds each with 50% overlap. Electrical noise was removed using notch filter centered at 50 hz. Next, baseline wandering was removed by implementing multilevel 1D wavelet decomposition of level 10, using 6th order Daubechies wavelet filter. 10th level approximated signal was subtracted from the original signal, smoothed and low-pass filtered (15 Hz cut off) using a 6th-order Butterworth filter. FIG. 4 illustrates result of pre-processing Body Surface Potential (BSP) signals. Then, cardiac potential was determined by using icEGM technique, where icEGM was reconstructed for 1998 atrial nodes and Root Mean Square Error (RMSE) was calculated against the 64 recorded endocardial potential. Optimized $\lambda$ value used in icEGM computation determined by L curve method was 0.932e-4. FIG. 5 illustrates the cardiac potential measurement along with key anatomical areas of the atrium (LA: Left atrium, RA: Right atrium, IVC: inferior venacava, SVC: superior venacava, LPV: Left pulmonary vein, RPV: Right pulmonary vein) and electrode measured EGM and icEGM from two specific nodes at left and right atria. RMSE for the reconstructed icEGM was in the range of 9 to 17%. Then, probable rotor regions were identified based on the cardiac potential. Further, the cardiac potential was used to estimate the power spectral density (PSD) after low pass filtering at 15 Hz cutoff with a 9th order Butterworth filter. PSD was obtained by implementing Welch periodogram over a 2 sec length window, with 50% overlap and 0.25 Hz resolution. Frequency with the largest peak in 3 to 15 Hz operating spectrum was considered as DF. Regularity Index and AF-DF probabilities were calculated. Only locations with AF-DF probability greater than 0.8 and normalized depolarization time greater than 0.85 were included to compute the final localization probability map.

Experimental Results and Observations

Figure 6A:
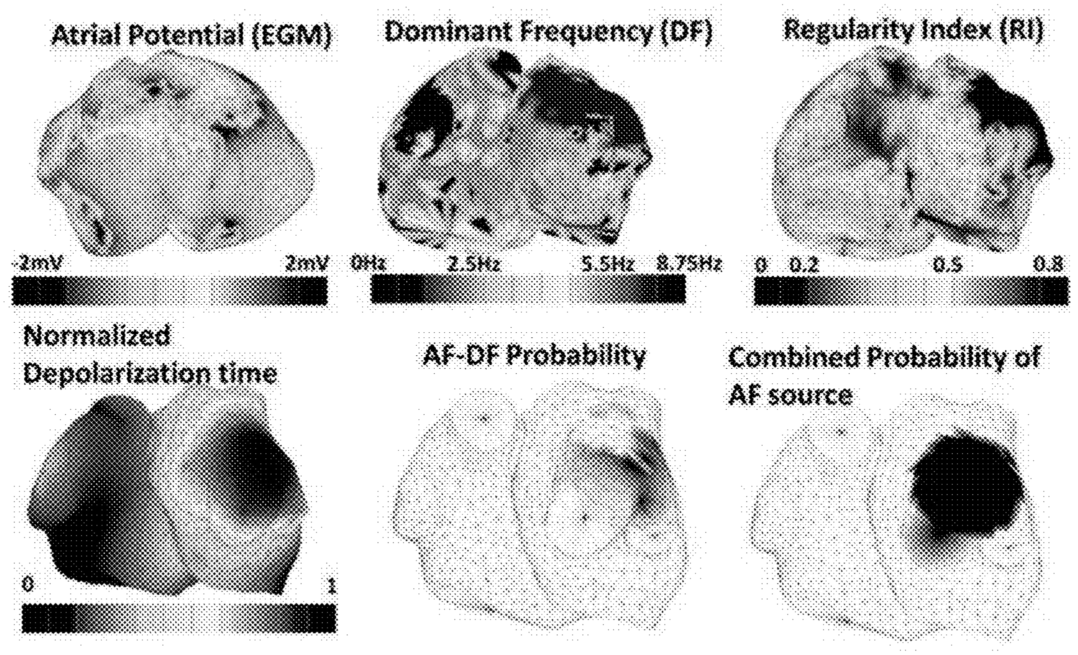
FIG. 6A illustrates metrics computed for source localization of AF on a simulated atrial dataset and corresponding node wise distribution is illustrated in FIG. 6B, according to some embodiments of the present disclosure.
Figure 6B:
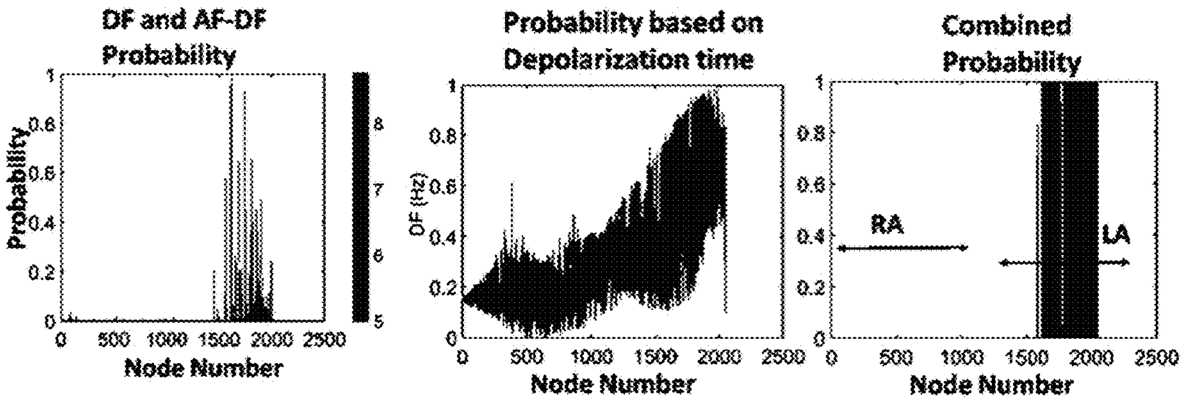

Experiments were performed on a simulated data set where ground truth rotor locations were known. This data set uses a realistic 3D atrial model to simulate atrial electrical activity, where activity of each node is modelled using ionic equations. For AF simulation, ionic currents and fibrosis distribution were varied to generate AF maintained by rotors that exhibits nonuniform propagation patterns. Atrial mesh consisted of 2048 nodes with 3 to 5 mm inter nodal distance. Simulated atrial EGM were processed at 500 Hz sampling frequency. AF episodes of 8 sec length were simulated by a single rotor located at left atrium at known node locations (around node number 1750 to 1950). Computed metrics were overlayed on 3D atrial geometry and visualized using Map3d software. FIG. 6A illustrates metrics computed for source localization of AF on a simulated atrial dataset and corresponding node wise distribution is illustrated in FIG. 6B, according to some embodiments of the present disclosure. FIG. 6A shows generated EGM on atrial surface, computed DF, RI, Normalized depolarization time, AF-DF probability and combined probability of AF source displayed on 3D atrial surface. Computed DF was in the range of 7.5 to 8.5 Hz in AF dominating regions and 5.5-6.5 Hz for other atrial regions. Although DF in nodes around 1800 to 1900 showed high frequency indicating rotor activities (figure showing node wise distribution of DF and AF-DF Probability, color axis), RI showed poor correlation with DF. Specifically in and around nodes of interest, RI value was quite low (range of 0.1-0.3) indicating low confidence in regions showing high DF. Depolarization time map shows very clean isochrones, with rotor region having highest depolarization. As the data is simulated and devoid of noises generated during inverse EP, depolarization time map provides higher accuracy than its spectral counterpart. AF-DF probability projects to regions of probable rotor sites and are matched better to ground truth compared to conventional DF-RI metric. Specially, non-AF regions were absolutely clean with focus only on probable rotor region which can be very beneficial while determining the search space for ablation region. As hypothesized, the combined metric of depolarization time and AF-DF was able to map rotor areas closer to the simulated AF regions.

Figure 7A:
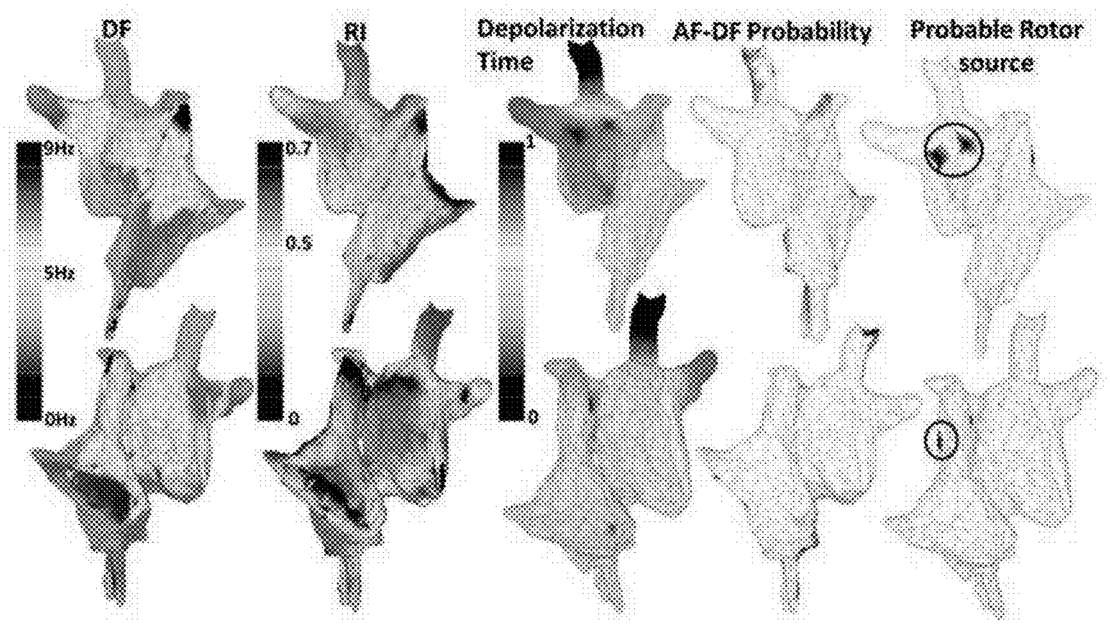
FIG. 7A illustrates metrics computed for source localization of AF on reconstructed patient atrial data and corresponding node wise distribution is illustrated in FIG. 7B, according to some embodiments of the present disclosure.
Figure 7B:
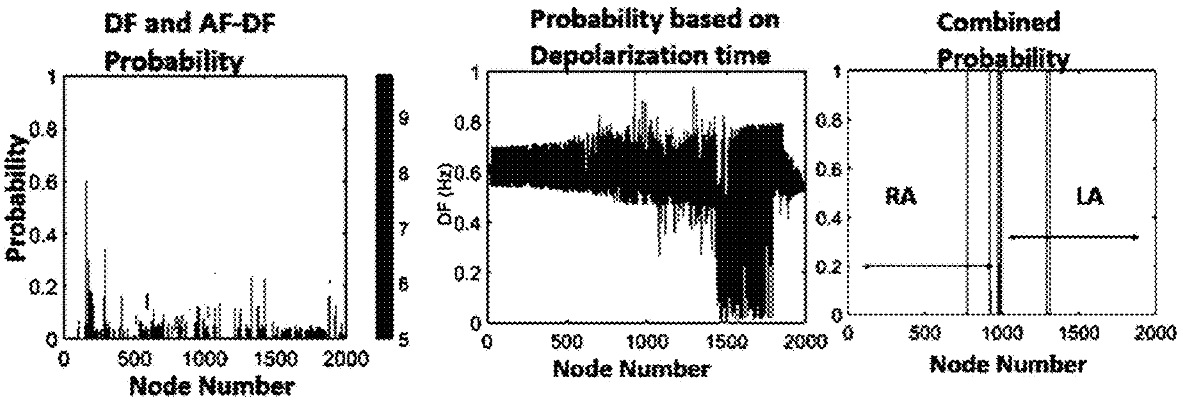

FIG. 7A illustrates metrics computed for source localization of AF on reconstructed patient atrial data from the EDGAR database and corresponding node wise distribution is illustrated in FIG. 7B, according to some embodiments of the present disclosure. From the FIG. 7A, it can be observed that the DF shows highest activation around 8 to 9 Hz with considerable amount of atrial area in 6.5 Hz to 7.5 Hz and some area around 5 Hz which is the base frequency range. Highest frequency values were mapped to some regions in upper RA and some areas around IVC (anterior view). PV areas in LA, which are medically most prone to be rotor areas also shows relatively high frequency in the range of 7.5 Hz. Some areas around lower left PV and right PV had frequency around 8 Hz. RI values, similar to trends observed in simulated data, did not show good correlation with computed high frequency regions. Most of the atrium, specially the posterior view regions reported low RI, indicating low confidence in computed DF. Depolarization time analysis shows highest activation in LA (areas between lower left and right PV, anterior view) and upper areas of right atrium (around SVC), posterior view). Areas around upper left PV showed minimum depolarization, unlike DF analysis which maps these areas into high frequency regions. AF-DF probability recomputes and adjusts probable regions around right atrium wall, IVC and some areas around left and right PV. The combined metric localized probable rotor areas around RA (SVC) and LA, just below PV (circled areas in FIG. 7A). As ablation data or ground truth is not available for this data, correctness of localized areas cannot be validated but comparison with prior art using same dataset shows close matching of DF metrics. Reconstructed atrial icEGM matched closely with recorded atrial EGM (FIG. 5) with RMSE value around 9 to 17%, which is comparatively less compared to state of art (Liberos A et.al. *Noninvasive Estimation of Epicardial Dominant High-Frequency Regions During Atrial Fibrillation. J Cardiovasc Electrophysiol.* 2016 Apr. Doi: 10.1111/jce.12931). The new metric AF-DF probability was able to better localize rotor areas compared to conventional DF-RI technique. Particularly with the current dataset, RI index did not provide good correlation with projected high frequency regions. Depolarization time as a metric to localize AF rotor have not been used in noninvasive approaches earlier. Computed normalized depolarization showed high accuracy in the simulated dataset. Although ground truth for EDGAR dataset is not available, the accuracy over simulated data set validates the usability of the method 200 for AF source localization. To summarize, rotor localization on the simulated data matched closely with the ground truth. For the patient data, localized areas were in accordance with state of art technique. Thus, the method 200 can provide better patient stratification for AF treatment plan, personalize procedure planning, and reduce ablation time.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:

obtaining, via one or more hardware processors, a plurality of heart scan images and a plurality of torso scan images;

extracting, via the one or more hardware processors, a) one or more atrial meshes from the plurality of heart scan images, and b) one or more torso meshes from the plurality of torso scan images;

sampling, via the one or more hardware processors, one or more Body Surface Potential (BSP) signals from the one or more torso meshes and the one or more atrial meshes, wherein the one or more BSP signals are pre-processed before identifying the one or more probable rotor regions by:

segregating the one or more BSP signals into a plurality of consecutive time windows;

removing noise from the one or more BSP signals in each of the plurality of consecutive time windows using a notch filter; and removing baseline wandering from the one or more BSP signals in each of the plurality of consecutive time windows using a multilevel 1-dimensional wavelet decomposition technique;

determining, via the one or more hardware processors, a cardiac potential from the one or more BSP signals;

identifying, via the one or more hardware processors, one or more probable rotor regions in the one or more atrial meshes based on the cardiac potential;

determining, via the one or more hardware processors, an Atrial Fibrillation-Dominant Frequency (AF-DF) probability based on the cardiac potential; and determining, via the one or more hardware processors, a probability of localizing AF source in the one or more atrial meshes by combining the identified one or more probable rotor regions and the AF-DF probability, wherein the one or more atrial meshes having the probability exceeding a threshold of the probability indicate locations of source of atrial fibrillation.

2. The method of claim 1, wherein identifying the one or more probable rotor regions in the one or more atrial meshes comprises:

computing a depolarization time from the cardiac potential; and identifying one or more atrial meshes having normalized value of the computed depolarization time greater than a predefined threshold value as the one or more probable rotor regions.

3. The method of claim 2, wherein computing the depolarization time from the cardiac potential comprises:

computing a temporal derivative of each of a plurality of atrial nodes in the one or more atrial meshes;

computing a second order spatial derivative of Laplacian of the cardiac potential; and combining the temporal derivative and the second order spatial derivative to obtain the depolarization time.

4. The method of claim 1, wherein determining the AF-DF probability comprises:

estimating power spectral density (PSD) from the cardiac potential;

arranging frequency values in the PSD in descending order; and calculating the AF-DF probability as normalized value of ratio of power at a peak frequency and power at a second peak frequency in the PSD.

5. A system comprising:

a memory storing instructions;

one or more communication interfaces; and one or more hardware processors coupled to the memory via the one or more communication interfaces, wherein the one or more hardware processors are configured by the instructions to:

obtain a plurality of heart scan images and a plurality of torso scan images;

extract a) one or more atrial meshes from the plurality of heart scan images, and b) one or more torso meshes from the plurality of torso scan images;

sample one or more Body Surface Potential (BSP) signals from the one or more torso meshes and the one or more atrial meshes, wherein the one or more hardware processors are configured to pre-process the one or more BSP signals before identifying the one or more probable rotor regions by:

segregating the one or more BSP signals into a plurality of consecutive time windows;

removing noise from the one or more BSP signals in each of the plurality of consecutive time windows using a notch filter; and removing baseline wandering from the one or more BSP signals in each of the plurality of consecutive time windows using a multilevel 1-dimensional wavelet decomposition technique;

determine a cardiac potential from the one or more BSP signals;

identify one or more probable rotor regions in the one or more atrial meshes based on the cardiac potential;

determine an Atrial Fibrillation-Dominant Frequency (AF-DF) probability based on the cardiac potential; and determine a probability of localizing AF source in the one or more atrial meshes by combining the identified one or more probable rotor regions and the AF-DF probability, wherein the one or more atrial meshes having the probability exceeding a threshold of the probability indicate locations of source of atrial fibrillation.

6. The system of claim 5, wherein the one or more hardware processors are configured to identify the one or more probable rotor regions in the one or more atrial meshes by:

computing a depolarization time from the cardiac potential; and identifying one or more atrial meshes having normalized value of the computed depolarization time greater than a predefined threshold value as the one or more probable rotor regions.

7. The system of claim 6, wherein the one or more hardware processors are configured to compute the depolarization time from the cardiac potential by:

computing a temporal derivative of each of a plurality of atrial nodes in the one or more atrial meshes;

computing a second order spatial derivative of Laplacian of the cardiac potential; and combining the temporal derivative and the second order spatial derivative to obtain the depolarization time.

8. The system of claim 5, wherein the one or more hardware processors are configured to determine the AF-DF probability by:

estimating power spectral density (PSD) from the cardiac potential;

arranging frequency values in the PSD in descending order; and calculating the AF-DF probability as normalized value of ratio of power at a peak frequency and power at a second peak frequency in the PSD.

9. One or more non-transitory machine-readable information storage mediums comprising one or more instructions which when executed by one or more hardware processors cause:

obtaining a plurality of heart scan images and a plurality of torso scan images;

extracting a) one or more atrial meshes from the plurality of heart scan images, and b) one or more torso meshes from the plurality of torso scan images;

sampling one or more Body Surface Potential (BSP) signals from the one or more torso meshes and the one or more atrial meshes, wherein the one or more BSP signals are pre-processed before identifying the one or more probable rotor regions by:

segregating the one or more BSP signals into a plurality of consecutive time windows;

removing noise from the one or more BSP signals in each of the plurality of consecutive time windows using a notch filter; and removing baseline wandering from the one or more BSP signals in each of the plurality of consecutive time windows using a multilevel 1-dimensional wavelet decomposition technique;

determining a cardiac potential from the one or more BSP signals;

identifying one or more probable rotor regions in the one or more atrial meshes based on the cardiac potential;

determining an Atrial Fibrillation-Dominant Frequency (AF-DF) probability based on the cardiac potential; and determining a probability of localizing AF source in the one or more atrial meshes by combining the identified one or more probable rotor regions and the AF-DF probability, wherein the one or more atrial meshes having the probability exceeding a threshold of the probability indicate locations of source of atrial fibrillation.

10. The one or more non-transitory machine-readable information storage mediums of claim 9, wherein identifying the one or more probable rotor regions in the one or more atrial meshes comprises:

computing a depolarization time from the cardiac potential; and identifying one or more atrial meshes having normalized value of the computed depolarization time greater than a predefined threshold value as the one or more probable rotor regions.

11. The one or more non-transitory machine-readable information storage mediums of claim 10, wherein computing the depolarization time from the cardiac potential comprises:

computing a temporal derivative of each of a plurality of atrial nodes in the one or more atrial meshes;

computing a second order spatial derivative of Laplacian of the cardiac potential; and combining the temporal derivative and the second order spatial derivative to obtain the depolarization time.

12. The one or more non-transitory machine-readable information storage mediums of claim 9, wherein determining the AF-DF probability comprises:

estimating power spectral density (PSD) from the cardiac potential;

arranging frequency values in the PSD in descending order; and calculating the AF-DF probability as normalized value of ratio of power at a peak frequency and power at a second peak frequency in the PSD.

* * * * *